(12) United States Patent
Zenhausern

(10) Patent No.: US 7,115,229 B2
(45) Date of Patent: Oct. 3, 2006

(54) APPARATUS AND METHOD FOR MONITORING MOLECULAR SPECIES WITHIN A MEDIUM

(75) Inventor: Frederic Zenhausern, Skillman, NJ (US)

(73) Assignee: Alpha MOS, Toulouse (FR)

( * ) Notice: Subject to any disclaimer, the term of this patent is extended or adjusted under 35 U.S.C. 154(b) by 588 days.

(21) Appl. No.: 09/961,904

(22) Filed: Sep. 24, 2001

(65) Prior Publication Data

US 2002/0094531 A1    Jul. 18, 2002

Related U.S. Application Data

(62) Division of application No. 09/332,659, filed on Jun. 14, 1999.

(51) Int. Cl.
*G01N 15/06* (2006.01)
*C12Q 1/68* (2006.01)
*C07H 21/04* (2006.01)
*G06K 9/00* (2006.01)

(52) U.S. Cl. .............. 422/68.1; 422/58; 422/119; 435/6; 435/7.1; 435/7.2; 435/7.3; 435/7.4; 435/287.1; 435/288.2; 435/288.3; 435/320.1; 435/252.8; 435/174; 435/183; 382/129; 382/133; 382/153; 382/173; 382/286; 382/291; 536/22.1

(58) Field of Classification Search .............. 435/6, 435/7.1, 7.2, 7.3, 7.4, 287.1, 288.2, 288.3, 435/320.1, 252.8, 174, 183; 422/58, 68.1, 422/119; 382/129, 133, 153, 173, 286, 291; 536/22.1
See application file for complete search history.

(56) References Cited

U.S. PATENT DOCUMENTS

| | | | | |
|---|---|---|---|---|
| 3,710,933 | A | * 1/1973 | Fulwyler et al. | ............. 209/3.1 |
| 5,015,843 | A | 5/1991 | Seitz et al. | |
| 5,386,115 | A | * 1/1995 | Freidhoff et al. | ........... 250/281 |
| 5,465,608 | A | 11/1995 | Lokshin et al. | |
| 5,571,568 | A | * 11/1996 | Ribi et al. | .................. 427/487 |
| 5,837,196 | A | 11/1998 | Pinkel et al. | |
| 5,866,430 | A | * 2/1999 | Grow | ........................ 436/172 |
| 6,100,026 | A | * 8/2000 | Nova | ............................ 435/6 |
| 6,259,373 | B1 | * 7/2001 | Ghahramani | ............. 340/815.4 |
| 6,312,893 | B1 | * 11/2001 | Van Ness et al. | ............... 435/6 |
| 6,485,703 | B1 | * 11/2002 | Cote et al. | .................... 424/9.1 |

* cited by examiner

*Primary Examiner*—Jezia Riley
(74) *Attorney, Agent, or Firm*—Fox Rothschild LLP

(57) ABSTRACT

Apparatus and methods for monitoring, analyzing, and/or discriminating molecular species, preferably a biomolecule, within a medium using a multisensor array (MSA) and multivariate processing. Biological compounds such as nucleotides and polynucleotides can be detected and analyzed. A reaction process such as an accumulation cycle of nucleic acids can be monitored, analyzed, and controlled using a multisensor array (MSA) and multivariate processing. Monitoring a biomolecule includes interrogating the medium, and preferably its gas phase, by coupling a sensor responsive to any changes of the medium and or biomolecule and its secondary products when, for example, an amplification reaction is proceeded. It is also a scope of the present invention to use direct detection and monitoring of biomolecular reactions in real-time without radioactive or fluorescent labeling. A preferred application is real-time polymerase chain reaction (PCR) detection.

7 Claims, 7 Drawing Sheets

APPARATUS AND METHOD FOR MONITORING MOLECULAR SPECIES WITHIN A MEDIUM

This application is a division of U.S. application Ser. No. 09/332,659, filed on Jun. 14, 1999.

FIELD OF THE INVENTION

The invention relates to an apparatus having a combination of multiple sensing probes or at least one multiple sensing probe and multivariate methods for monitoring and/or discriminating between molecular species, preferably biomolecules, within a medium preferably during a reaction process such as an accumulation cycle of nucleic acids.

BACKGROUND OF THE INVENTION

Several sensor technology developments have been described in the art. In particular, arrays of semiconductor sensors having sensitive and chemically-diverse interface materials capable of interacting with analytes of complex mixtures have previously been used. These can incorporate many operating principles including: doped tin-oxide gas sensors, doped conductive polymers, field effect transistor (FET) devices, and optical fiber devices.

Some sensors are based on a more specific chemical adsorption. For example, enzymes or antibodies can provide a more selective response when incorporated with sensors such as immunoFET's, redox enzyme electrodes, ion-channel simulating devices or antibody-coated piezoelectric or surface acoustic wave devices [review by Gardner J. W., Bartlett P. N., *Sensors Actuators*, B18–19, 211–220, 1994]. Recently, mass sensing quadrupole transducers (e.g., using mass spectrometers (MS)) have been commercially available for the application in food quality control. MS can analyze sample headspace [U.S. Pat. No. 5,363,707 to Augenblick, et al.].

Generally, multisensor arrays do not include only biosensors. All the wells of a 96 well plate can be viewed concurrently with a charge coupled device (CCD) camera. For example, see Atwood in U.S. Pat. No. 5,766,889. One example of DNA detection by arrays of biosensors uses a fiber optic bundle to screen or analyze a surface enhanced Raman scattering (SERS) surface [U.S. Pat. No. 5,814,516 to Vo-Dinh, Tuan]. Another example of biosensor arrays uses a fiber optic bundle modified with compounds that bind biological species [U.S. Pat. No. 5,837,196 to Pinkel, Daniel]. These examples do not use multivariate processing. Furthermore, these examples have large complex fiber optic bundles. Better MSAs (though not necessarily optical) have smaller and easier to replace sensors. This is important due to fouling of the sensors surfaces.

Other work and examples of devices used in the art of chemical sensing are described into the following references, which illustrate some of the major transducing systems such as (i) resonant microstructures [U.S. Pat. No. 5,025,346 to Tang, Williams C. and Howe, Roger T.; U.S. Pat. No. 5,445,008 to Wachter, Eric A. and Thundat (using a micro-cantilever), Thomas G.; Barnes J. R., et al., *Rev. Sci. Instrum.*, 65(12), 3793–98, 1994], (ii) amperometric, conductivity/capacitance sensing platforms [U.S. Pat. No. 5,801,297 to Mifsud J. -C. and Moy L.] or (iii) optical detection [U.S. Pat. No. 5,563,707 to Prass Werner, et al.,; U.S. Pat. No. 5,512,490 to Walt David R. and Kauer John S.; U.S. Pat. No. 5,004,914 to Vali, Victor, et al.; U.S. Pat. No. 5,436,167 to Robillard Jean J.; U.S. Pat. No. 5,015,843, Seitz, William R. and McCurley, Marian F.].

In particular, the last approach can be illustrated by the development efforts of Walt, et al. [Dickinson T. A., White J., Kauer J. S., Walt D. R., *Nature*, 382, 697–700, Aug. 22, 1996] employing a miniaturized array of fibers containing a special fluorescent dye (Nile Red) embedded in a polymer matrix. Such a strategy is based on the use of a dye exhibiting large wavelength shifts in its strong fluorescent response to various vapors. The dye is photochemically stable and can be immobilized in polymers. The art uses a configuration of nineteen 300 µm optical fibers with their flat sensing ends coated with the dye (i.e., Nile Red) encapsulated in various polymers. A video frame grabber permits fluorescent intensity versus time data to be recorded. From the variations in response time and the individual fiber light output, the system can be trained to recognize these differences and identify specific vapors. One particular problem with the above-described system involves the photobleaching of the dye molecules. This limits the reliability and reproducibility of the sensor system.

Efforts to date in the art of gas sensor technology have centered upon the field of applications of the detection of toxic substances and smells for the evaluation of odor properties in consumer products, environmental science, and medicine [U.S. Pat. Nos. 5,801,297 and 5,563,707]. For example, microorganism detection in the manner described by Payne, et al. in U.S. Pat. No. 5,807,701, uses an array of conducting polymer sensors to sample vapor associated with the microorganisms. Payne discloses detection of organisms, but not of biomolecules and/or PCR products.

Almost all analytical techniques or process monitoring techniques are based on one or two variables at a time. For example, these variables can be an analytical signal representing absorbance, chromatographic retention time, or electrochemical response. These variables can be time-based as in process control. These traditional analytical techniques usually give acceptable results when analyzing simple systems with only a few components with variables (e.g., analytical signals) that do not interact with each other. Multicomponent mixtures such as solutions, gases, solids, process streams, effluents, and contents of reaction chambers usually have many variables that interact with each other. For example, absorbance peaks of several components can overlap each other. These variables should be analyzed simultaneously to optimize the useful analytical data that would be obscure in traditional analytical techniques.

As explained below, multicomponent mixtures or solutions can be analyzed by a multivariate analysis based on the reference data. {H. M. Heise, A. Biftner, "Multivariate calibration for near-infrared spectroscopic assays of blood substrates in human plasma based on variable selection using partial least squares (PLS) regression vector choices, Fresenius' Journal of Analytical Chemistry, 362(1) (1998) 141–147}. Nonlinear multivariate calibration methods have been reviewed by Sekulic, et al. (Analytical Chemistry, 65 (1993) 835A–845A).

Multivariate analysis techniques include many artificial intelligence techniques. Some examples include artificial neural networks (ANN), expert systems (ESs), fuzzy logic (FL), genetic algorithms (GAs). ANNs learn by training. ESs are based on defined rules. FL systems are based on uncertainty and partial truths. These techniques can be used in concert. New techniques will also be developed, and are contemplated to be used in this invention.

Isidore Rigoutsos and Andrea Califano in U.S. Pat. No. 5,752,019 and related references describe a family of new techniques using probabilistic indexing algorithms such as Fast Look-up Algorithm for String Homology (FLASH), hash algorithms, and data mining algorithms. Paul Stolorz, et a/. describe Bayes algorithms (also called Bayesian statistical methods) in "Predicting Protein Secondary Structure Using Neural Net and Statistical Methods" *J. Mol. Biol.* 225 (1992) 363.

Multivariate analysis reconstructs analytical data from several variables. Multivariate process monitoring handles noise and drift better with fewer false alarms than univariate monitoring. For example, multivariate analysis can determine an analyte's concentration from several of its absorbance peaks. Theoretically, multivariate analysis can be applied to most analytical and process control techniques. Examples include: fluorescence, chromatography, absorption spectroscopy, emission spectroscopy, X-ray methods, radiochemical methods, nuclear magnetic resonance spectroscopy, electron spin resonance spectroscopy, surface science techniques, refractometry, interferometry, mass spectrometry, gas density, magnetic susceptibility, electrochemistry, surface acoustic wave sensors, sensor arrays, ultrasonic sensors, and thermal analysis.

Multiple variables can be converted into useful analytical data by multivariate analysis. This multivariate analysis or multivariate technique can relate instrumental response to the concentrations, physical, chemical, or physico-chemical properties at several wavelengths. The most commonly used multivariate techniques with FTIR spectroscopy are classical least squares (CLS) and inverse least squares (ILS). CLS is a limited method in the sense that the concentrations of all component analytes must be known exactly. ILS is a wavelength limited method because the number of wavelengths used must be smaller than the number of samples. These two methods lack the power to handle data with similar spectral features. {D. Qin and P. R. Griffiths, SPIE, 2089, p. 548 (1994)}. There are also the factor-based or bilinear projection methods of PLS, sometimes called Projection to Latent Structures, Principal Components Analysis (PCA), and Principle Components Regression (PCR). PLS is a good technique for process control when both process and product data are used to control the process. {Stone, M. Brooks, R. J. (1990) "Continuum Regression: Cross-validated Sequentially Constructed Prediction Embracing Ordinary Least Squares, Partial Least Squares and Principal Components Regression", Journal of the Royal Statistical Society B, 52, 237–269}. Nonlinear Principle Components Regression (NLPCR) and Nonlinear Partial Least Squares (NLPLS) can model nonlinear responses. {Sekulic, et al., Analytical Chemistry, 65 (1993) 835A–845A}. Soft Independent Modeling of Class Analogy (SIMCA) is another of several more multivariate methods.

The results of the multivariate analysis are usually used directly to give concentration values for the measured analyte. Multivariate techniques can be used for infrared and near-infrared spectroscopy. See James M. Brown, U.S. Pat. No. 5,121,337; Bruce N. Perry, et al., U.S. Pat. No. 5,641,962. Perry, et al. claim non-linear multivariate methods. Multivariate techniques can be used for hyphenated chromatography like GC-MS. Ashe, et al., U.S. Pat. No. 5,699,270. Multivariate techniques can be used for surface acoustic wave (SAW) vapor sensors. Lokshin, et al. U.S. Pat. No. 5,465,608. Some references describe applying other properties to the data such as octane values. Bruce N. Perry, et al., U.S. Pat. No. 5,641,962; Maggard, U.S. Pat. No. 5,349,189, freezing point depression in milk, Arnvidarson et al., U.S. Pat. No. 5,739,034, and cancerous stages of tissue samples Haaland et al. U.S. Pat. No. 5,596,992. There is little art on fitting the data from multivariate analysis to an algorithm to determine other properties. For example, there is little art on joining multivariate analysis with monitoring of any PCR process.

DNA and similar large biomolecules are hard to detect in gas phase. These large biomolecules are hard to volatilize and are subject to degradation. There are only a few methods that can safely break up large biomolecules into detectable fragments such as fast atom bombardment (FAB) and Cf-252 mass spectrometry. For example, see "Fragmentation of Proteins in the 13–29 kDa Mass Range Observed by 252Cf-Plasma Desorption Mass Spectrometry" D. M. Bunk, and R. D. Macfarlane. Proc. Nat. Acad. Sci. (USA) 89 (1992) 6215. Other methods use thermospray or electrospray. For example see Kaufman et al. in "Analysis of Biomolecules using Electrospray", *J. Aerosol Sci.*, 29, p. 537 (1998). and by Jarell, J. A. and Tomany, M. J. in U.S. Pat. No. 5,828,062. Combining these methods would greatly benefit the detection of large biomolecules such as DNA and RNA.

The Polymerase Chain Reaction (PCR) technique was devised by Kary Mullis in the mid-1980s and, like DNA sequencing, has revolutionized molecular genetics by making possible a whole new approach to the study and analysis of genes. A major problem in analyzing genes is that they are rare targets in a complex genome that in mammals may contain as many as 100,000 genes. Molecular genetics techniques currently used to overcome this problem are very time-consuming, involving cloning and methods for detecting specific DNA sequences. The Polymerase Chain Reaction has changed all this by enabling production of enormous numbers of copies of a specified DNA sequence without resorting to cloning.

The Polymerase Chain Reaction (PCR) exploits certain features of DNA replication. DNA polymerase uses single-stranded DNA as a template for the synthesis of a complementary new strand. These single-stranded DNA templates can be produced by simply heating double-stranded DNA to temperatures near boiling. DNA polymerase also requires a small section of double-stranded DNA to initiate ("prime") synthesis. Therefore the starting point for DNA synthesis can be specified by supplying an oligonucleotide primer that anneals to the template at that point. In this important feature of the PCR, DNA polymerase can be directed to synthesize a specific region of DNA.

Both DNA strands can serve as templates for synthesis, provided an oligonucleotide primer is supplied for each strand. For a PCR, the primers are chosen to flank the region of DNA that is to be amplified so that the newly synthesized strands of DNA, starting at each primer, extend beyond the position of the primer on the opposite strand. Therefore new primer binding sites are generated on each newly synthesized DNA strand. The reaction mixture is again heated to separate the original and newly synthesized strands, which are then available for further cycles of primer hybridization, DNA synthesis, and strand separation. The net result of a PCR is that the end of n cycles, the reaction contains a theoretical maximum of $2^n$ double-stranded DNA molecules that are copies of the DNA sequence between the primers. This second important feature of PCR results in the "amplification" of the specified region.

A number of amplification reaction amplification reaction assays have been developed, such as the Polymerase Chain Reaction (PCR) described above and in the following references [N. Amheim, H. Erlich, *Ann. Rev. Biochem.*, 1992, 61, pp. 131–56; U.S. Pat. Nos. 4,683,202; 4,683,195; and U.S. Pat. No. 4,985,188 to Mullis, Kary]. In most commonly used sequencing methods, a target-specific sequence is amplified by enzyme cycle reactions ultimately effecting an increase in the amount of amplification unit or amplicon produced. In addition to the target sequence of a typical amplification, additional components and/or reagents can be consumed limiting the amplification of PCR products. Several improvements of the standard PCR method have been reported into literature for various specific applications, such as in-situ, reverse transcriptase, hot start, long and accurate or even touch down methods [Dan R. H., Cox P. T., Wainwright B. J., Baker K., Mattick J. S., 1991, "Touchdown PCR to circumvent spurious priming during gene amplification", Nucleic Acids Res., 19, 4008; Rodriguez I. R., Mazuruk K. S., Schoen T. J., Chadler J. G., 1994, "Structural analysis of the human hydroxindole-O-methyl transferase gene: presense of two district promoters", J. Biol. Chem., 269, 31969–31977; Birch D. E., Kolmodin L., W. J., McKinney N., Wong J., Young K. K. K., Zangenberg G. A., Zoccoli M. A., "Simplified hot start PCR", Nature 381, 445–446, 1996]. Among such efforts to date in the prior art, and for the sack of clarity, standard PCR is described in the present invention. Currently, the most common methodology for PCR involves sample preparation having a master mix and primers [Mullis K. B; Faloona F. A; Scharf S; Saiki R. K; Horn G; Erlich H. A., Specific enzymatic amplification of DNA in vitro: the polymerase chain reaction. *Cold Spring Harbor Symposia on Quantitative Biology*, 1986; and Scharf S. J; Horn G. T; Erlich H. A. Direct cloning and sequence analysis of enzymatically amplified genomic sequences. *Science*, Sep. 5, 1986, 233(4768):1076–8.], followed by detection and analysis of the reaction products. Real-time quantitative monitoring of PCR kinetics have been reported [Higuchi R; Fockler C; Dollinger G; Watson R. Kinetic PCR analysis: real-time monitoring of DNA amplification reactions. *Biotechnology* NY, September, 11(9), 1026–30 (1993)] but one important drawback is the requirement for target-specific fluorogenic probes. Several labeling strategies have been reported into literature including radiolabeling, enzyme-linked colorimetry [Yu, H., et al., Cyanine Dye dUTP Analogs for Enzymatic Labeling of DNA Probes, *Nucleic Acids Research*, 22 (15), pp. 3226–3232, 1994], silver staining, fluorescent staining, and chemoluminescent staining [Zhu, Z., et al., Directly labeled DNA probes using fluorescent nucleotides with different length linkers, *Nucleic Acids Research*, 22 (16), pp. 3418–3422, 1994].

Higuchi, et al. [1993] described an assay for any amplifiable DNA sequence that uses a video camera to monitor multiple polymerase chain reactions (PCRs) simultaneously over the course of thermocycling. The video camera detects the accumulation of double-stranded DNA (dsDNA) in each PCR using the increase in the fluorescence of ethidium bromide (EtBr) that results from its binding with duplex DNA. The kinetics of fluorescence accumulation during thermocycling are directly related to the starting number of DNA copies. The fewer cycles necessary to produce a detectable fluorescence, the greater the number of target sequences. Results obtained with this approach indicated that a kinetic approach to PCR analysis can quantitate DNA sensitively, selectively, and over a large dynamic range. A commercially available system was developed for real-time PCR assay exclusively exploiting the fluorescence measurement of a pair of reporter-quencher fluorescent probes during thermal cycling reaction [U.S. Pat. Nos. 5,723,591 and 5,210,015].

The basic stages of PCR typically comprise: (1) synthesis of primers complementary to a target piece of DNA, (2) separating strands of DNA target by thermal cycling and attaching primers to each end of the target sequence, (3) extending strands by adding ATP and the enzyme polymerase and then repeating the above steps typically after 25–30 cycles until the replication produces a useful amount of target DNA (e.g., $10^8$ copies). The widespread way to check for the presence of these fragments of DNA of defined length is to load a sample taken from the reaction product, along with appropriate molecular-weight markers, onto an agarose gel which typically contains 0.8–4% Et Br.

DNA bands are then visualized under UV illumination and identification of any product can be done by comparing product bands with reference bands of known molecular-weight markers [Sambrook, et al., *Handbook Mol. Biol.*, Spring Harbor; Gelfand, D. H. and White, T. J., *In PCR Protocols, A Guide to Methods & Applications*, ed. M. A. Innis, D. H. Gelfand, J. J. Sninsky, T. J. White, 129–41, New-York Academic Press, 1990]. More recently, developments have been reported into the prior art and in particular the introduction of automated DNA synthesizer and new synthesis reagents exploiting multiple fluorophore markers for which changes in fluorescent signal can be proportional to the number of amplification cycles [*Handbook of Fluorescent Probes and Research Chemicals*, 1996, $6^{th}$ edition, Molecular Probes Inc. Eugene Oreg.; PCR Systems, Reagents and Consumables, Perkin-Elmer catalog, 1996–1997].

Atwood discloses determination of concentration growth of nucleic acids in PCR using a group of concurrent reaction vessels monitored concurrently by a charge coupled device (CCD) camera [U.S. Pat. No. 5,766,889 to Atwood, John G.]. Atwood discloses a label-based fluorescence technique.

PCR is the basis of many of today's biotechnology advances. Any improvement in the PCR process has an enormous impact on our lives through biotechnological advances. A MSA combined with a multivariate process would drastically improve PCR performance. Improvements can include better time control, better selectivity, higher purity and lower error rates by not exclusively using tags, and lower cost.

References listed herein are incorporated by reference.

SUMMARY OF THE INVENTION

The invention relates to a method for monitoring and/or analyzing a molecular species, preferably biomolecules, within a medium preferably during a reaction process such as an accumulation cycle of nucleic acids. Generally, a biomolecule is detected, but a tag detached from the biomolecule or a medium surrounding a biomolecule may also be detected. It is also within the scope of the present invention to use direct detection and monitoring of biomolecular reactions in real-time without radioactive or fluorescent labeling. In a preferred embodiment, a multiple sensor array (MSA) is used as the detector. Multivariate analysis is used to extract useful information from the detector. The useful information can be used to control the measured process and/or reaction. A preferred application is the control of a polymerase chain reaction (PCR).

The present invention relates to a method and device for the detection and/or monitoring of a biomolecule within a medium preferably having some reagents and nucleic acids, and/or organic molecules, by using an assembly of at least one probing element for monitoring, preferably odorous, biomolecules or at least one secondary product of the biomolecule in gaseous and/or liquid form. Four classes of biological molecules are known, namely, proteins, lipids, carbohydrates and nucleic acids. Other biological materials such as antigens (either soluble or as components of bacteria or viruses), antibodies, or receptor molecules can be monitored or screened within the scope of this invention. One of the more significant applications comprises nucleic acids that, in turn, comprise two subclasses: DNA which is a genetic component of all cells, and RNA which usually functions in the synthesis of proteins.

The scope of the present invention generally extends to biomolecules. Examples of biomolecules include nucleic acids, proteins, lipids, and carbohydrates. The preferred embodiment extends to DNA biomolecules having DNA components. DNA is emphasized because it is the prime genetic material, carrying all hereditary information within chromosomes. A gene normally exists as two strings of nucleotides entwined in a helical shape resembling a spiral staircase. There are four DNA nucleotides, adenine (A), cytosine (C), guanine (G) and thymine (T). The sequence of these nucleotides in a gene encodes the information a cell uses to build a specific protein. Based upon the importance and potential consequences of the characterization of the genome of humans and selected model organisms, as well as many others of deeply scientific and commercial interest, it appears that enormous improvements in sequencing technology are needed to satisfy high-throughput sequencing initiatives.

The present invention provides a method and apparatus for a direct fast detection and monitoring of an unlabelled biomolecule cycling or amplification reaction.

In a preferred embodiment, a multivariate detector can preferably comprise an array of sensing devices which might be using similar or different transducing mechanisms. As it has been described earlier in the present application, several sensing devices can be used to monitor a biomolecule amplification reaction. In particular, an assembly of a few metal oxide electrodes (e.g. $SnO_2$) can have some of their physico-chemical properties modified when they are exposed to a medium comprising a biomolecule and/or reagents and/or by-products. Such modifications can be probed with and electronic means generating a set of output variables which are then processed and analyzed using multivariate algorithms. Such a means is defined as a multivariate detector.

With respect to PCR applications, the present invention obviates the exclusive requirement of attaching a fluorescent probe by preferably detecting any volatile substance by using at least one chemical sensor. Either an intercalator-based probe (e.g., ethidium bromide) where a chemical is intercalated within the double helix, or any of a component or secondary product from the master mix, buffer, primer or DNA molecule itself can be detected. This approach also provides a means of determining the effect of different reaction conditions on the efficacy of the amplification and so can provide insight into fundamentals and quality control of PCR processes.

It is also within the scope of the present invention to offer a novel alternative technology for measuring a threshold cycle of PCR amplification (e.g., DNA, RNA) that preferably combines a non-gel based detection, preferably using a number of gas sensors often organized in arrays, and a recognition means (e.g., pattern recognition) typically exploiting multivariate analysis algorithms (e.g.; PCA, DFA, SIMCA, PLS). Representative examples are described above. The embodiment described further in this invention can achieve either end-point measurement or real-time detection of molecular species such as PCR products during their accumulation cycle. The preferred time period between detection samples is less than about 70 milliseconds. This real time detection does not have to include analysis time.

Although PCR is this invention's preferred embodiment, other reactions are contemplated. Enzymatic cascades can be considered as amplification or cyclic reaction to produce an output. Replication of viruses or bacteria is also within the scope of the invention through the monitoring of the replication of genetic material. For example, monitoring of alive bacteria versus dead bacteria via MSA detection can compete with light scattering measurements described by Mark Taubenblatt in U.S. Pat. No. 5,061,070. This invention detects organisms indirectly by detecting the organism's contents. Accessing these contents generally requires breaking or penetrating the organism's outer wall (e.g., cell wall or protein casing).

This invention covers measurement in solid (e.g., temperature, mass, cantilever, and tactile measurements), liquid, gaseous, and vapor (e.g., aerosol) phases. Solid phase sensing is rare. Liquid phase measurements tend to be prone to sensor fouling. Immersed sensors also tend to have less selectivity than gas or vapor phase sensors. By measuring in the gas or vapor phase, MSAs can have an added layer of selectivity base on which molecules enter the gas or vapor phase. In this way, the contents of a headspace can be a subset from the contents of the condensed phase it is in contact with.

Based on the needs for improvement, it is also within the scope of this invention to monitor an amplification reaction of preferably PCR products with the use of at least one sensor capable of being responsive to any change of its photophysical and chemical properties by influence of surface interactions. Preferably, electroluminescence and photoluminescence quenching or spectral shifts of porous silicon sensor material [Sailor, M. J., Lee, E. J., *Advanced Materials*, 9(10), 783–793, 1997; U.S. Pat. No. 5,453,624 to Sailor, Michael J. and Doan, Vincent V.] should permit simple and cost-effective device fabrication for use in actual PCR application. The pore diameter affects the wavelength. There is no photobleaching as with dyes and both wavelength and wavelength shifting can be measured. All references above are incorporated herein by reference in their entirety.

The biotech, chemical, and pharmaceutical industries have been waiting for a technique to use the direct detection and monitoring of biomolecular mechanisms (e.g., amplification reaction of PCR products) without radioisotopic labeling or photolabeling (i.e., fluorescence or chemiluminescence). The present invention relates to a method and apparatus for detecting preferably a biomolecule as it undergoes an amplification reaction. This invention is primarily motivated by the industrial need for a highly-sensitive assay capable of monitoring the presence, and possibly the concentration of various molecular species in an environment. For the sake of clarity, the following detailed description of the invention is referring to nucleic acids, preferably DNA.

The invention thus relates to monitoring, analyzing, and/or discriminating between molecular species, preferably biomolecules, within a medium using a multisensor array (MSA) and multivariate processing. Analytes are also discriminated from the medium. Biological compounds such as nucleotides and polynucleotides can be detected and analyzed. A reaction process such as an accumulation cycle of nucleic acids can be monitored, analyzed, and controlled using a multisensor array (MSA) or at least by measuring several physico-chemical properties of a probe, and multivariate data processing. Monitoring a biomolecule includes interrogating the medium, and preferably its gas phase, by coupling a sensor responsive to any changes of the medium and or biomolecule and its secondary products and/or byproducts when, for example, an amplification reaction is proceeded. It is also a scope of the present invention to use direct detection and monitoring of biomolecular reactions in real-time without radioactive or fluorescent labeling. A preferred application is in real-time polymerase chain reaction (PCR) detection.

DETAILED DESCRIPTION OF THE INVENTION

Figure 1:
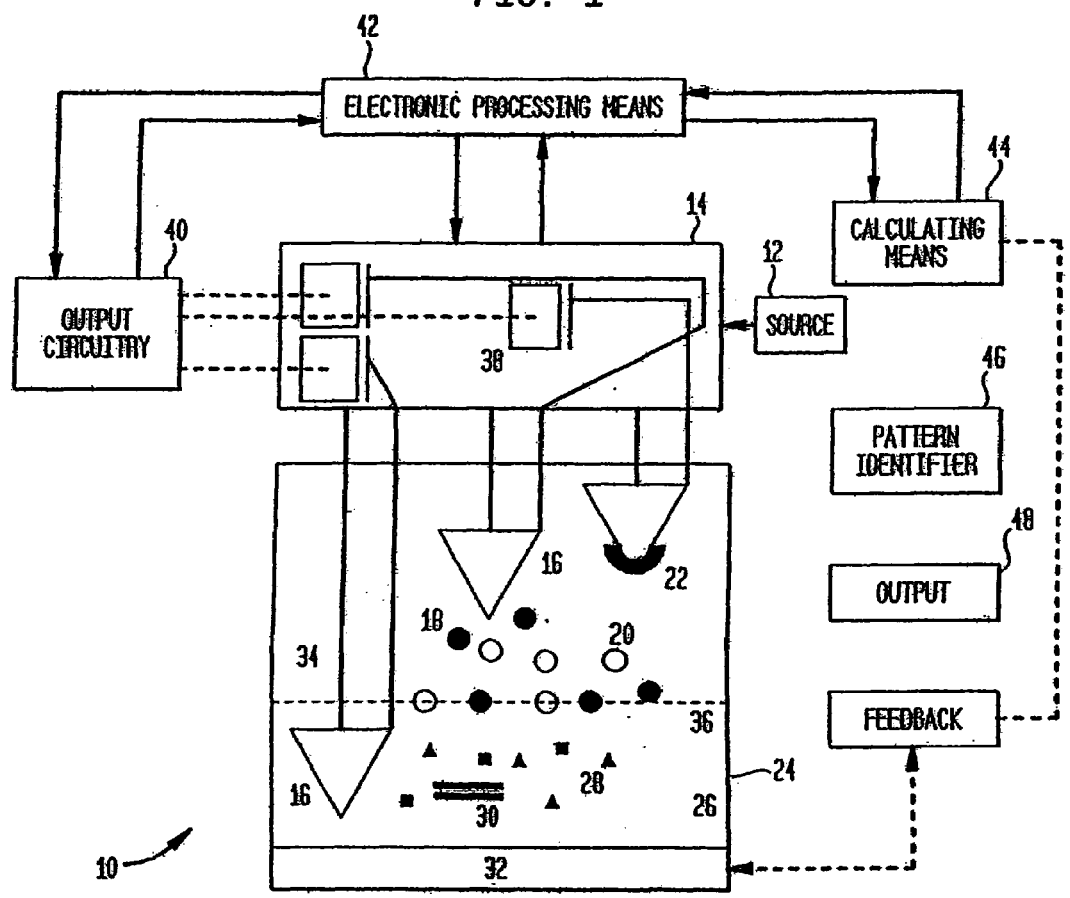
FIG. 1 is a schematic drawing of an assembly suitable for monitoring and optionally controlling a biomolecule or a secondary product of the biomolecule.

The invention relates to apparatus and methods for monitoring information in a medium having at least one biomolecule. The medium is screened or analyzed (preferably in its gas phase) by coupling a sensor responsive to any changes of the medium and or biomolecule and its secondary products and/or byproducts when, for example, an amplification reaction is proceeded. A method and apparatus for monitoring the vapors of a volatile part (e.g., tag or solvent) of the carrier or in combination with a biomolecule such as a nucleic acid is described herein.

In particular, the invention pertains to the method for monitoring information in a medium, the medium having at least one biomolecule, the method having the steps of screening the medium with a screening means having a n number of sensing probes, where n is an integer of at least one so that more than one physical, chemical, or physicochemical change which defines the information is detected by the probe to produce at least one signal output; transferring the signal output to a signal processing means responsive to differences in electromagnetic properties of the signal for generating a final output; receiving the final output into a pattern recognition means sufficient to generate a measurement pattern of the information being operable to define a set of class boundaries; and sorting the information in accordance with the class boundaries representative of the presence and preferably quantitative amounts of biomolecule in the medium. The medium can be a gas or a liquid or a solid or a combination of several phases. The medium can have at least one of organic or inorganic reagent.

The n number of sensing probes can be a multiple sensor array. The n number of sensing probes can also be at least one semiconductor gas sensor, doped metal oxide gas sensor or an undoped metal oxide gas sensor used in gas or vapor phase, conductive polymer sensor, vibrating or resonant micromechanical device, mass spectrometer, or optical sensing probe (e.g., an optical fiber, apertured probe, and/or apertureless probe). The sensing probe can also have one or more coatings.

The information can be at least one of odorous or volatile chemical species characteristics of the presence of the biomolecule or the part of the biomolecule. At least part of the information detected by the probe can be changes in the concentration of the biomolecule, a secondary product of the biomolecule, a radiative property of the electromagnetic spectrum of the biomolecule, a non-radiative property of the electromagnetic spectrum of the biomolecule, or a non-radiative property of the electromagnetic spectrum of a secondary product of the biomolecule.

The multivariate analysis can be principal components analysis, deterministic finite-state automata, or partial least squares. The multivariate analysis can be trained, or supervised, or untrained, or unsupervised. The signal processing means can be a frequency analyzer.

This method can further have the steps of obtaining a multivariate analysis reference model based on the signal output; and screening an analyte selected from the group consisting of a biomolecule, a biomolecule fragment, a biomolecule byproduct, a medium, a reagent, and a tag, to predict the property of the biomolecule. This method can also further have the step of comparing the class boundaries with properties of a second group of signal outputs.

An apparatus for analyzing at least one biomolecule in a medium, having a multivariate detector having at least one of a sensing probe, sensing location, or physicochemical property, said multivariate detector capable of detecting at least the biomolecule, a byproduct, or a secondary product thereof, and discriminating the biomolecule, the byproduct, or the secondary product from the medium; transmission means, capable of transmitting a signal between the multivariate detector and a data acquisition system, capable of converting the signal into raw data; a computational device capable of processing at least part of the raw data using multivariate analysis to create a data set; and an output device capable of displaying, storing, or using the data set. The output device can be or include a feedback control capable of using the data set to control a biological replication process. This analyte can be DNA or a fragment thereof, and the feedback can control a polymerase chain reaction in approximately real time.

A process controller for controlling a biological replication process, having a multisensor array having more than one sensing location capable of detecting a nucleotide or polynucleotide, discriminating the nucleotide or polynucleotide from the medium, and generating an output; a computational device capable of processing the output using multivariate analysis to create a data set; and a feedback control capable of using the data set to control the biological replication process. This analyte can be DNA or a fragment thereof, and the feedback can control a polymerase chain reaction in real time.

An apparatus for screening at least one of a cell, bacteria, a bacteriophage, or a virus in a medium, having: a multisensor array having at least one sensing location capable of detecting a nucleotide or polynucleotide that is extracted from the bacteria, bacteriophage, or virus; means for discriminating the nucleotide or polynucleotide from the medium; means for generating an output; a computational device capable of processing the output using multivariate analysis to create a data set; and an output device capable of displaying, storing, or using the data set.

An apparatus for analyzing at least one of a cell, a bacteria, a bacteriophage, or a virus in a medium, having: a multisensor array with more than one sensing location, the array capable of detecting a molecule created or modified by the bacteria, the bacteriophage, or the virus, discriminating the molecule from the medium, and generating an output; a computational device capable of processing the output using multivariate analysis to create a data set; and an output device capable of displaying, storing, or using the data set. This apparatus can analyze at least one of DNA, RNA, AIDS, a nucleotide, a biomolecule, or cancer.

The above specific medium types sensor probe types, analysis types, analyte types, and information types are preferred embodiments of this invention and only the claims should limit this invention.

In one embodiment (illustrated by FIG. 1), the system includes at least one sensing device and circuitry (i.e., electronics) for monitoring an induced signal. The degree of accumulation of biomolecules, such as the progress of the amplification reaction of PCR products, is determined from the measurements of the excitation and induced electrical and/or optical signal generated at an interfacial zone of at least one sensing device. It will be appreciated that the sensing device may be relatively uniform or have different sensing areas. An assembly or hybrid of similar or different sensing devices may also be used. Other systems and methods may be employed, such as the use of mass spectrometry (MS) for the analysis of the sample headspace, providing a sensing apparatus and methodology for detecting and evaluating at least one analyte alone or in an admixture during at least one extension phase of amplification reaction.

In a preferred embodiment, the apparatus relates to an assembly of components having at least one sensing element for detecting a biological analyte of interest in gaseous, vapor, and/or liquid form, and a recognition progression pattern means by which to discriminate and/or identify and archive that analyte of interest.

An MSA is made up of at least two different sensors. Often each sensor in the array has its own signal connection and its own sensitivity. However, other MSA configurations are possible. For example, one can scan a sensor with a non-uniform sensing surface.

Sensors can be based on many different technologies. Examples include, but are not limited to: sensor materials, sensing mechanisms, communications methods (e.g., wireless), sensing discrimination, and useful lives. The invention can use many technologies including, but not limited to: metal oxide semiconductor (MOS), quartz crystal microbalance (QCM), mass spectrometry (MS), surface acoustic wave (SAW), aperture (e.g. fiber optical sensors) or apertureless optical sensors (e.g. sharp resonant microcantilevers such as the ones used in AFM), interferometric sensors, scanning probe techniques and its modifications (e.g., porous silicon, photoluminescent, and GaAs), chemically-sensitive field effect transistors (chemFET), electrochemical sensors, sensors modified with conductive polymers, and pressure sensors. Scanning probe techniques include methods and instruments such as atomic force microscopy (AFM), scanning tunneling microscopy (STM), and scanning interferometric apertureless microscopy (SIAM). Apertured probes, including many fiber optics probes, use lenses and are diffraction limited. Apertureless probes, such as probe antenna and SIAM {Wickramasinghe, et al., in U.S. Pat. Nos. 5,646,731 and 5,538,898; and Zenhausern, et al. in *Science,* 269, pp. 1083–1085 (1995)}, use local perturbation of electromagnetic fields instead of lenses.

A sensing probe can be any sensor, instrument or other means for detecting chemical, physical, or physico-chemical changes of a biomolecule, part of a biomolecule, or their related by-products, solvents, medium, reagents, and. environment.

Resonating or vibrating sensing probes are defined as micromechanical devices such as SAW, QCM, AFM cantilevers, and materials with piezoelectric properties. Resonating sensing probes are preferred. These sensing probes can be coated with materials such as polymers, ion exchange resins (e.g., perfluorosulfonated ionomers called PFSIs), porous silicon, optical reflectors, silanes, thiols, oxides, absorbants, selective coatings, chromatographic solid phases (e.g., for gas chromatography), hydrocarbons, elastic coatings, hygroscopic materials, cage materials (e.g., buckyballs and fullerene tubules), crown materials (e.g., crown ethers), or nucleotides. The coating can be in thin films, monolayers, sub-monolayers, self-assembled monolayers (SAM) and other formats. Part of the coating can contain binders, and/or physical fillers.

Liquid phase MSA detectors can often be less sensitive due to the usually higher analyte concentrations found in a liquid compared to a vapor. In comparison, gas phase detection usually offers an added level of selectivity by monitoring liquid to gas transitions and less surface contamination (i.e., longer useful life and often faster response time). Combining volatilization methods such as mass spectrometry or electrospray with a gas phase MSA (often called an electronic nose) would greatly benefit the detection of large biomolecules such as DNA and RNA.

Multivariate analysis can be based on many different technologies including, but not limited to: classical least squares (CLS), inverse least squares (ILS), partial least squares (PLS), principal components analysis (PCA), principle components regression (PCR), nonlinear principle components regression (NLPCR), nonlinear partial least squares (NLPLS), deterministic finite-state automata (DFA), FLASH, pattern recognition, and neural networks. The multivariate analysis can be trained/supervised by teaching it what signals to use based on theory or analyte samples of known parameters. Alternatively, multivariate analysis can be untrained/unsupervised.

A preferred embodiment of the invention involves the detection and/or analysis of nucleotides and polynucleotides. The nucleotides and polynucleotides can be either directly and/or indirectly sampled. Direct sampling would detect the biomolecule or part of it. Indirect sampling methods include, but are not limited to, sampling the medium, sampling a tag on the nucleotide, sampling the headspace, and sampling the biomolecule itself.

In another preferred embodiment, bacteria, bacteriophages, viruses, and cellular material can be analyzed by sampling the nucleic acids (e.g. nucleotides, polynucleotides, proteins, lipids, and/or carbohydrates) that they contain. Generally, this sampling must follow the disruption of the cell wall or envelope around the nucleotide in a statistically relevant sample. Alternatively, bacteria, bacteriophages and viruses in a medium can be analyzed by sampling changes in the medium. For example, changes in alcohol or sugar concentration is proportional to living yeast concentration in a fermentation process.

Viruses, bacteriophages, bacteria and other organisms are difficult to detect by conventional chemical sensors or biosensors. They can be detected by mass (e.g., by QCM), but are difficult to differentiate from the medium. It would be advantageous to break up the outer envelope (e.g., cell wall or protein casing), so that the internal biomolecules can be liberated and typically the genetic biomolecule can be detected by an MSA. In the preferred embodiment of this use of the present invention, at least some of the genetic materials of viruses and bacteria is detected. It would be beneficial to create a new technique to measure live versus dead bacteria to compete with light scattering techniques.

Figure 2:
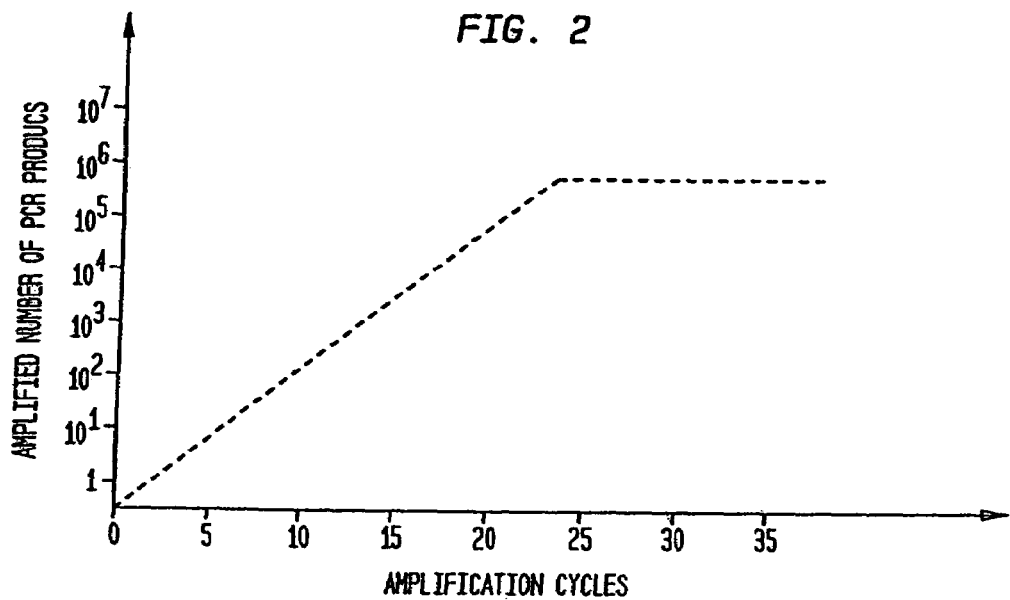
FIG. 2 shows a diagram of a growth curve preferably representative of a PCR amplification reaction.

The apparatus and methods may be employed to detect DNA replication by polymerase chain reaction (PCR). FIG. 2 shows the basic stages of PCR which can typically comprise: (1) synthesis of primers complementary to a target piece of DNA, (2) separating strands of DNA target by thermal cycling and attaching primers to each end of the target sequence, (3) extending strands by adding ATP and the enzyme polymerase and then repeating the above steps typically after 25–30 cycles until the replication produces a useful amount of target DNA (e.g., $10^8$ copies).

A still further object of the invention is the provision of a new type of chemical labeling of preferably nucleic acids and peptides exploiting the use of volatile reagents. For example, in the case of peptide sequencing, the method can be similarly performed as an Edman degradation or derivatization using, for example, trifluoroethyl isothiocyanate (TFEITC).

The method can be adapted to generate derivatized products for analysis by multisensor arrays (MSAs) such as, for example, solid-state semiconductor sensors, optical fiber, and mass spectrometers, as follows:

First, experimental conditions are optimized in order to decide how many cycles of sequence are needed, an aliquot of the sample is removed. A cycle of Edman degradation on the aliquot is performed, using, for example, TFEITC, to generate the n-1 peptide. Then an equivalent aliquot is added to the first one, and the Edman degradation is repeated to produce the n-1 and n-2 peptides. After repeating the process several times, the peptide mixture is analyzed by MSA, and the differences in the fingerprints of the sensor array output are compared allowing the classification of the various cycles and/or copies number. Then, the system can be trained to recognize such patterns (e.g., artificial intelligence algorithm such as neural networks or high-dimensional indexing algorithms such as in U.S. Pat. No. 5,577,249 to Califano, et al.) allowing interrogation of an unknown sample to determine its number of copies. The use of some end-terminal (amino or nucleotide) tagging reagents (e.g., a quaternary ammonium alkyl-N-hydroxysuccinimide ester, pyridine analogous) that enhances the detection of volatile compounds during, for example, a PCR cycling reaction is also suitable for use in the invention.

The invention relates generally to the in-situ monitoring of an amplification reaction of one or more biomolecules using a multisensor array (MSA) or at least one sensor with several possible physical and/or chemical responses for detecting some volatile compounds.

For example, in the case of PCR analysis, the prior art describes approaches requiring labeling of the biomolecules with fluorescent tags. The most widespread methods are the dideoxy chain termination method, e.g., Sanger et al., *Proc. Natl. Acad. Sci.*, vol. 74, pp. 5463–5467 (1977) and the chemical degradation method, e.g., Maxam, et al., *Proc. Natl. Acad. Sci.*, vol. 74, pp. 560–564 (1977). For automated applications, other ways of analyzing the chain termination have been reported (e.g., Sanger, et al., *J. Mol. Biol.*, vol. 143,161–178 (1980)).

Because of the novelty of the present embodiment, some of the severe constraints relative to the use of fluorescent labels (e.g., requiring four spectrally resolvable dyes, photobleaching, quantum efficiency, etc.) can be overcome by employing any volatile compound either consumed in a reaction, and/or producing by-products, or linked to a target substance such as the nucleic acid fragments of a PCR reaction. For example, base labeling procedures known from the prior art can be used with the invention. Preferably, a linking group between a base-linker-base can be formed by reacting an N-hydroxy ester (NHS) of a volatile organic tag of the invention according to methods taught in the prior art (e.g., U.S. Pat. Nos. 4,997,928 and 5,262,536, both to Hobbs, Jr., Frank W.).

Preferably, classes of volatile organic tags identified in accordance with the invention are defined in terms of volatile compounds having a molecular weight of between 50 and 350 g/mole. More preferably, the classes arise in the following types of chemicals such as (C2–C6) aliphatic acids, lactic acid, acetic acid, pyridine, 3-hydroxy-2-butanone, propionic acid, iso- and n-butyric acid, phenylacetaldehyde, furfuryl alcohol, isovaleric acid, α-methyl butyric acid, dimethylsulfone, n-dodecanol, n-hexadecanol, p-cresol, indole, benzaldehyde, benzoic acid, ethylene glycol, propylene glycol or any chemical derivatization procedure used in gas-phase DNA analysis.

In a particular PCR application of the present invention, any volatile chemical or mixtures thereof consumed in a reaction medium can also generate an indirect signal representative of the evolution of the reaction of the biomolecule detectable with the apparatus of the invention. The previous description of preferred volatile species suitable for practicing the invention has been presented only for purposes of illustration and description. It is not intended to be exhaustive or to limit the scope of the invention to the precise form disclosed. Obviously many modifications and variations are possible in light of the above teaching by those skilled in the art.

Monitoring is often performed by comparing a pattern generated by any change in output signal other set of detected data of any sensor to a reference pattern and/or discriminated from any other pattern. It is not known or obvious outside the present instruction, how one may perform monitoring, and in particular direct monitoring, of unlabelled PCR products, preferably in real-time, when the PCR reaction proceeds. The present invention addresses and solves this problem by way of preferred novel assemblies suitable for quantitative and/or qualitative measurement of amplification PCR products (preferably) and/or, secondary products or byproducts, or chemical changes of a mixer medium containing the products. The present invention has also as an object to allow a high throughput method of about 300 samples per day which represents a two orders of magnitude improvement in speed compared to conventional Northern blot assays.

FIG. 1 shows a schematic diagram and is not drawn to scale. FIG. 1's entire assembly 10 shows the physical components that preferably may be assembled in realization of the present invention. The assembly 10 preferably includes an electromagnetic source 12 (e.g., power supply or laser) driving a detector means 14 (encompassing the entire box attached to sensors 16) having preferably several probes 16 arranged in an array. The probes 16 can either exhibit similar physico-chemical properties or preferably slightly different chemical affinity response to various chemical species 18 and 20. The physico-chemical properties can comprise either bulk or surface properties of the probe material itself (e.g., silicon) or through its derivatization and/or coating with preferably a thin film of organic polymer matrix offering a semi-selective means capable of interrogating the medium components and/or biomolecule, preferably PCR fragments. The probe 16 may preferably comprise a near-field probe such as a sharp AFM tip [Zenhausern, F., et al., *Journal of Applied Physics*, 1992], a tapered optical fiber [U.S. Pat. No. 5,272,330 to Betzig, Robert E., et al.], a substrate and/or a quartz crystal microbalance or a mass sensitive detector such as a mass quadrupole. The probe 16 may have a coating 22 having an embedded dye (e.g., fluorophore or Nile Red) in a polymer matrix or layers of non conductive and conductive polymers [U.S. Pat. No 5,788,833 to Lewis, Nathan S.]. Other coatings are listed herein. The probe may be modified in other ways such as etching a silicon profiling tip at least partially converting the tip into porous silicon. Typically, a container 24 contains at least one medium 26 (e.g., liquid) with reagents 28 (e.g., enzymes, primers, one or more of the four deoxyribonucleotide 5' triphosphates (dNTP's), water and typical subcomponents of a PCR reaction mixture) and at least one biomolecule 30, preferably a target DNA template. The container 24 can also be thermally regulated with a thermal cycler bloc 32 (e.g., Peltier element) which can help convert at least one part of the sample into preferably a gas phase or headspace 34. The sample is preferably passed through a transmission element 36 (e.g., membrane or semi-permeable membrane) where various components 18 and 20 representative of the advancement of the PCR amplification reaction can be delivered to at least a proximity of a probe 16. The transmission element 36 also can be coupled to a sample carrier means preferably ending with a waste reservoir. Any disposing means such as a pressure pumping unit, electrophoresis, or chromatography (e.g., gas chromatography (GC), high pressure/performance liquid chromatography (HPLC) column chromatography, or capillary electrophoresis) can be added in conjunction with an appropriate closed environment and/or sensor technique (e.g., mass detector requiring vacuum). Typically, any interaction between any of products 18 and/or 20 with the probe 16 preferably arranged in an array allows to generate at a transducer 38, an electromagnetic signal wave (e.g., electrical, optical, or magnetic) representative of a change in at least one chemical, physical, or physico-chemical property of the probe 16 through, for example, a multipole coupling between the probe 16 and molecular products 18 and 20, or a spectral change or an intensity change in resistivity of the probe 16. For example, multiplexing of several signal waves and combining the signal waves in an output circuitry 40 can provide a signal output which can typically be processed by an electronic processing means 42 prior to be input in a calculating means 44 (e.g., computer) for preferably statistical comparison with a pattern identifier 46 (e.g., database software for archiving and graphical display) whose output generate a mapping of the components within the medium and/or biomolecule, preferably PCR products. For example, multivariate analysis, fuzzy logic, neural network, and other algorithms widespread in the prior art can be used to process any output patterns. An optional feedback and/or control system 50 can be added to control and/or automate and/or monitor the process.

As an example of the technique of the invention and with the aim of demonstration, the samples analyzed in FIGS. 7–12 were prepared according to standard procedures described in standard parvovirus PCR reaction protocols. Various PCR products were provided with a template copy (i.e., 0, 1, 10, 100, 1,000, 10,000 copies) and placed in a thermal cycler for the appropriate number of PCR cycles. Following cycling, 3 samples of each copy number were labeled with the number of cycles performed (i.e., 0, 1, 5, 15, 20, 30, 40 and 50 cycles). Concurrently, six master samples containing templates were prepared for each copy number amplification so that the same cocktails were used for all 8 cycle groups. Prior to sample screening, a fourth product replicate was retained by chromatography retention ligand (CRL) or affinity chromatography for each reaction condition and analyzed on an agarose gel to check amplification. The primers used for this PCR demonstration produced a 354 base pairs product in the presence of template. As it is conventionally practiced by those skilled in the prior art, PCR products were visualized by ethidium bromide staining for samples cycled 30, 40, and 50 times. In this procedure, it is also possible for single copy samples to be negative regardless of cycle number since end point dilutions may or may not contain a template copy. For example, see Table 1 in Example 1.

Heating can be by any method including microwave, radio frequency (RF), convection, conduction, and radiation. Heating modes can include methods such as ramping, DC pulse and/or AC pulse.

Figure 3:
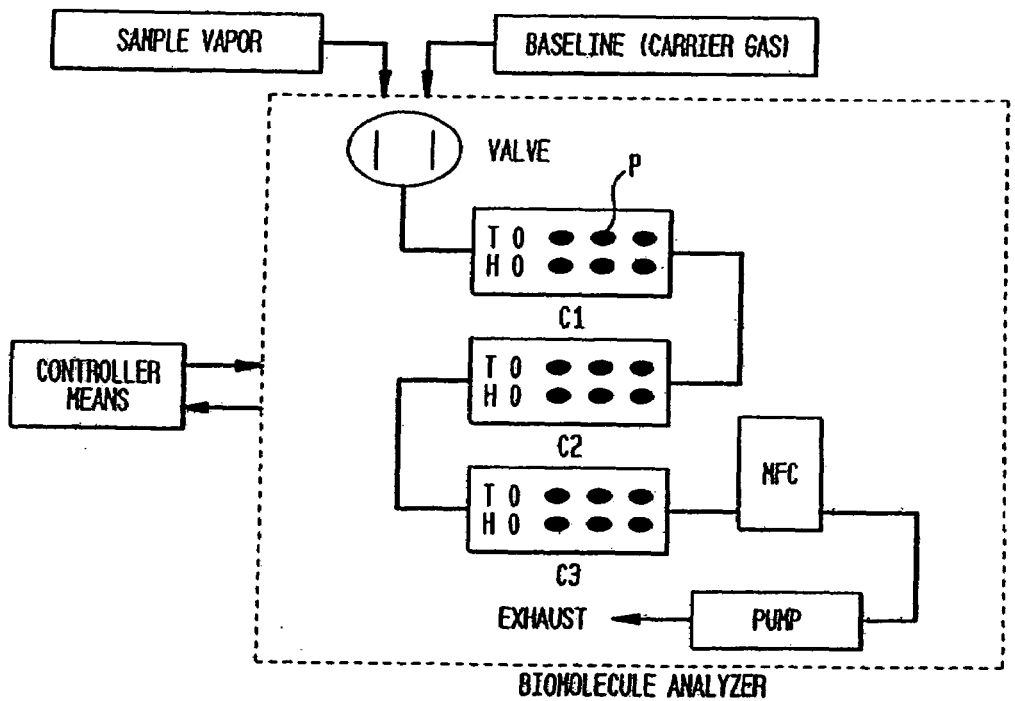
FIG. 3 shows a diagram of the biomolecule analyzer in a preferred embodiment used for demonstration and used to generate the results shown in FIGS. 5–8.

FIG. 3 shows the operation of the biomolecule analyzer (indicated by the dashed line) used as a demonstration of one preferred embodiment. Prior to sampling, the medium containing a biomolecule, reagents and/or secondary products is placed in a container, preferably a sealed vial. It is then agitated, and/or slightly heated (below denaturation temperature of the biomolecule) to generate a sample headspace representative of the medium and biomolecule, which are preferably PCR products. A volume of the sample headspace (or sample vapor) is preferably extracted by a thermally regulated syringe from an autosampling apparatus and, for example, flow injected into a carrier gas flow. The flow is typically carrying the sample through preferably a few chambers (C1, C2, and C3) having several sensing elements (P). Typically the flow can be generated and maintained by a mass flow controller (MFC) unit and, for example, a pump can carry the analyzed sample to an exhaust or waste reservoir. Any induced changes in, for example, sensor resistances are monitored. The humidity and temperature in the chambers are monitored during the operation by probes labeled H and T, respectively. The controller means preferably comprises a computer with data acquisition and signal processing components.

Figure 4:
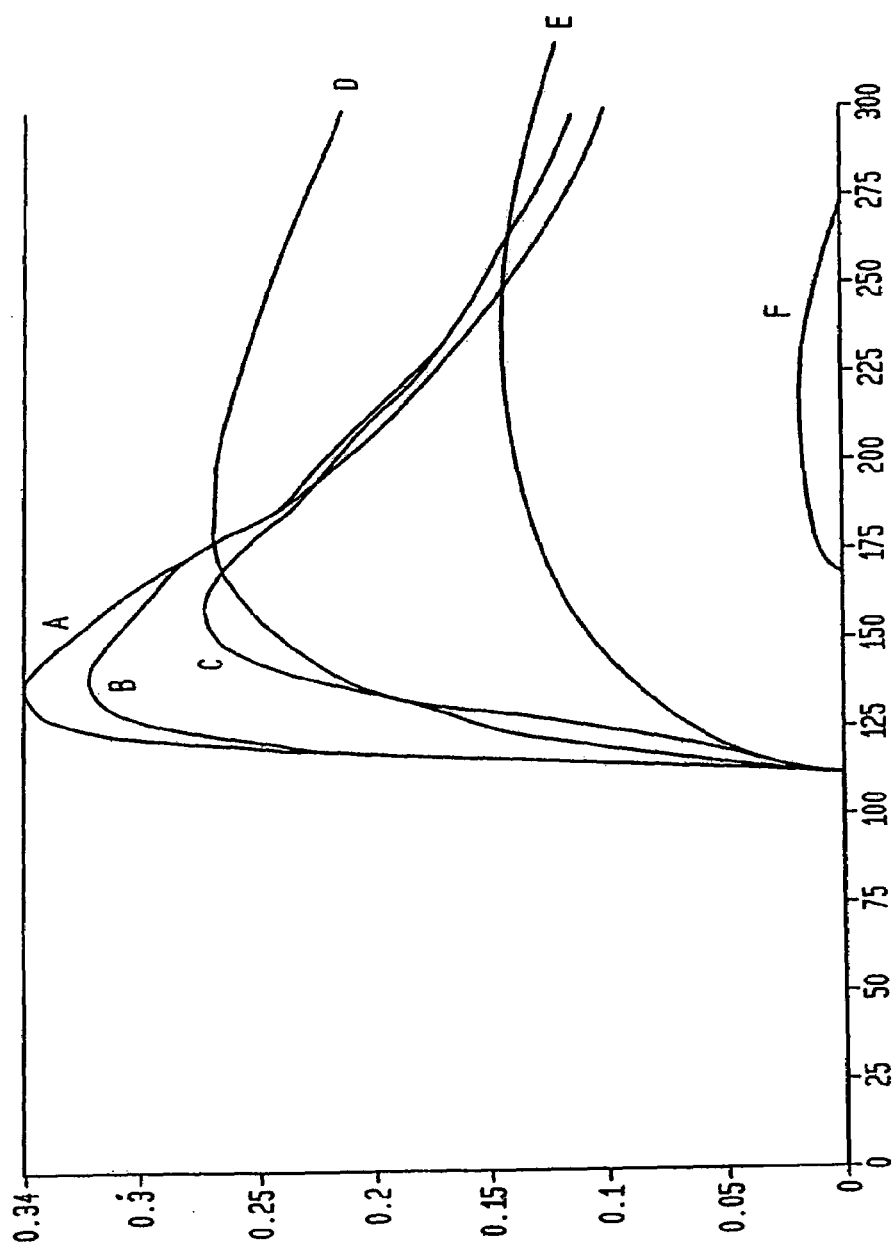
FIG. 4 shows a graph illustrating the sensor response of several sensors, preferably semiconductor-based (e.g., tin dioxide doped and/or undoped) when they are interrogating some chemical compounds and preferably a mixture of PCR products and reagents.

FIG. 4 shows a graph of individual responses of multiple sensors when exposed to the medium having a biomolecule. Each individual sensor is labeled A, B, C, D, E and F. The x axis is time in seconds. In this example, the Y axis is the normalized change in sensor resistivity. These responses comprise several of the data points used in FIGS. 5–8. FIG. 4 illustrates the percentage of response (Y axis) as a function of time (X axis). Typically, between each measurement, the system pauses until the sensor outputs return to their original state or start resistance. A computing system is preferably coupled to the system of FIG. 3 allowing control feedback and data collection in view of generating an output pattern which can be indicative of the presence and/or identity of the medium or PCR products. This pattern is, for example, compared with stored patterns representing a collection of known PCR products.

A preferred procedure is for preparing a biomolecule, such as a DNA fragment, for screening in conjunction with the present sensing system. A sample is prepared by adding a volatile emissive agent that can be actively incorporated into the biomolecule (or into the reaction medium of the biomolecule undergoing amplification) to produce a mix of labeled biomolecules and/or products. The biomolecule or emissive products in the medium can then be detected by typically and preferably an array of gas sensors (i.e., an MSA for detecting gases).

While there have been described a method and apparatus for monitoring a molecular species in a medium, and using a multiple sensor array (MSA) for detecting gases, it will be apparent to those skilled in the art that modifications and variations are possible to such systems without deviating from the broad principle of the present invention.

Figure 5:
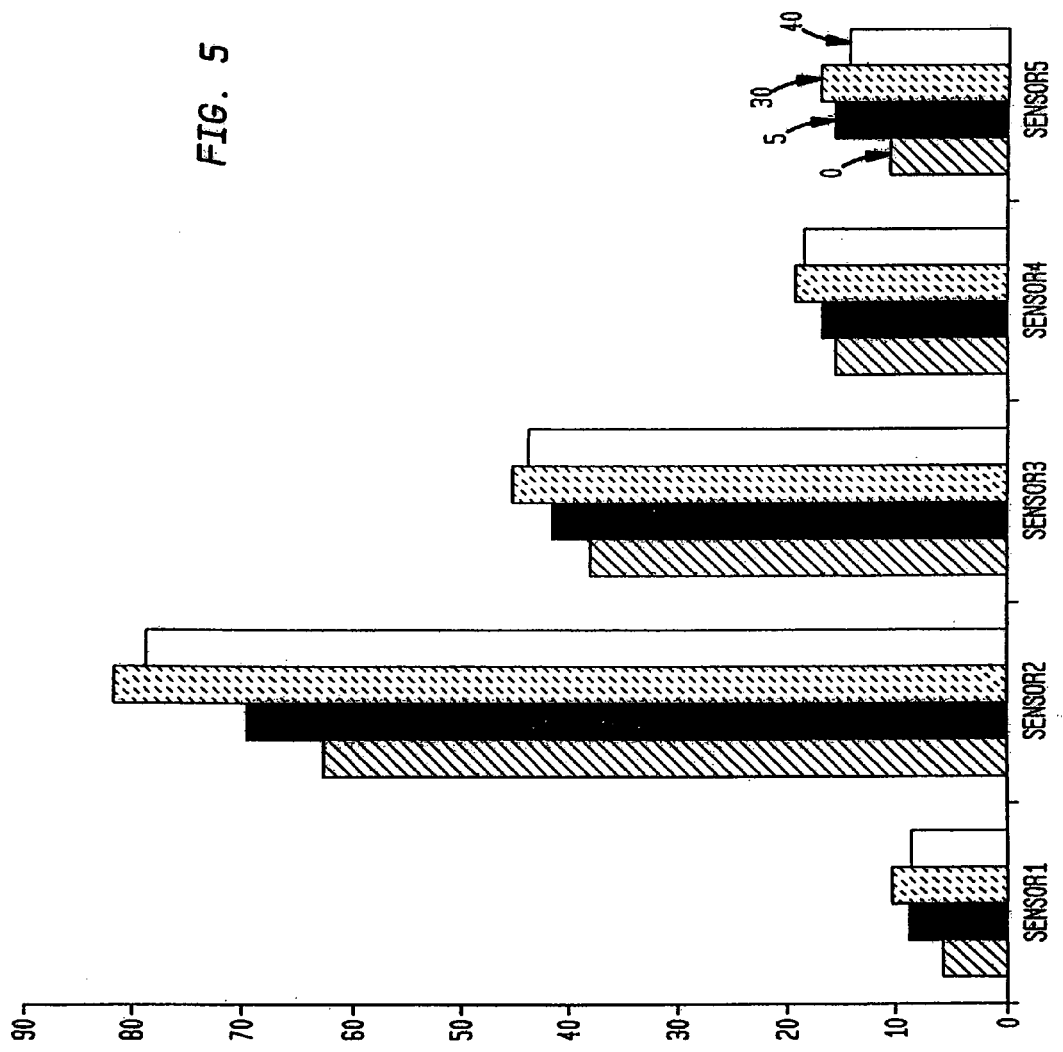
FIG. 5 shows various sensor responses preferably electrical signals during and/or after exposure to the reagents and PCR products mixtures during and/or after a few amplification reaction cycles providing the pattern.

FIG. 5 is a bar chart representing the different response of the six sensors shown in FIG. 4 to the PCR amplification or reaction cycles 0, 5, 30 and 40 (respectively from left to right). For example, the dark black bar represents cycle 5. The response of sensor 2 is larger than the responses of sensors 1, 3, 4, and 5. This large response of sensor may enhance the discrimination by having a larger weighting factor calculated in the multivariate algorithm.

Figure 6:
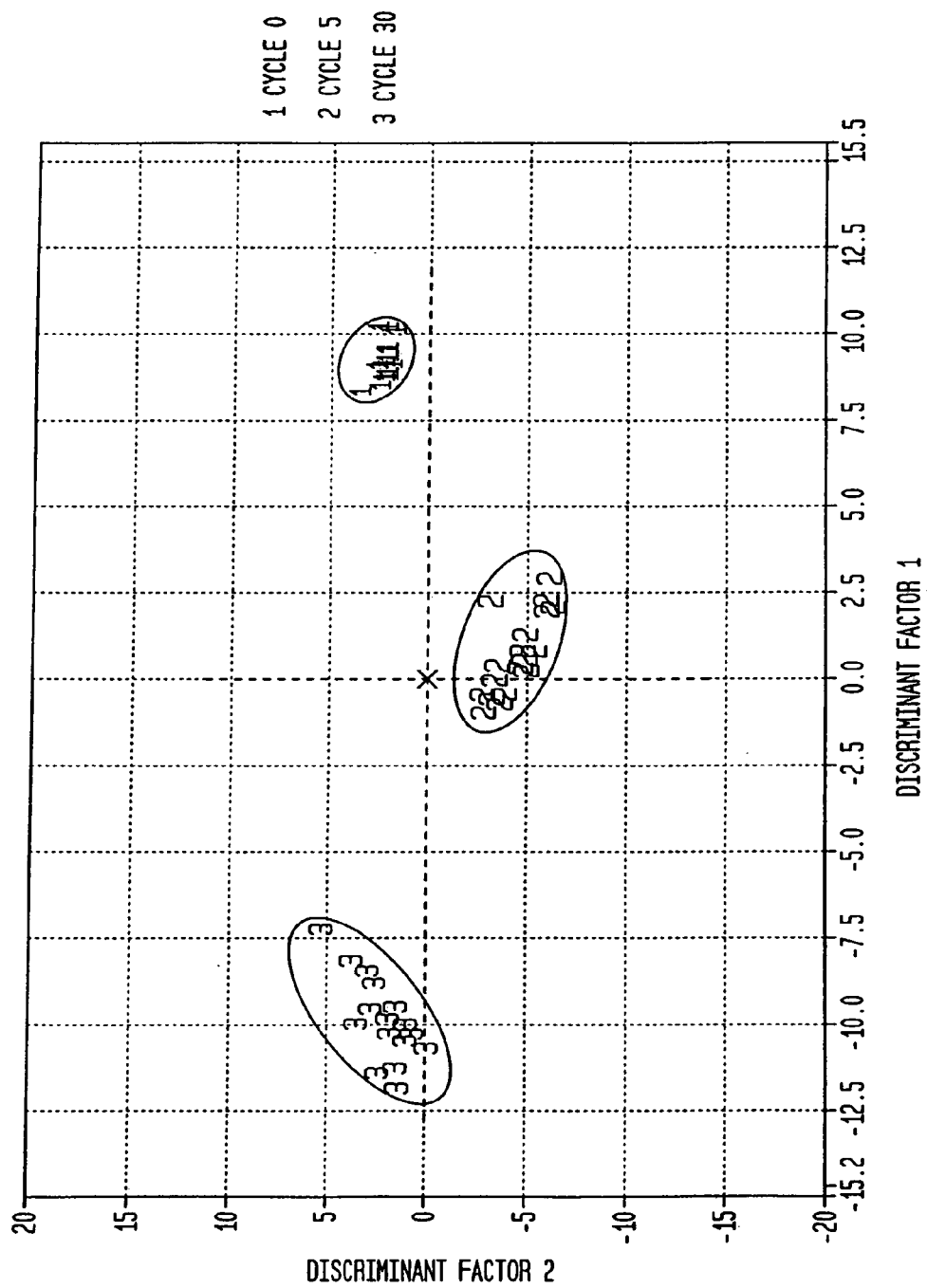
FIG. 6 shows a DFA plot of PCR reaction cycles 0, 5 and 30.
Figure 7:
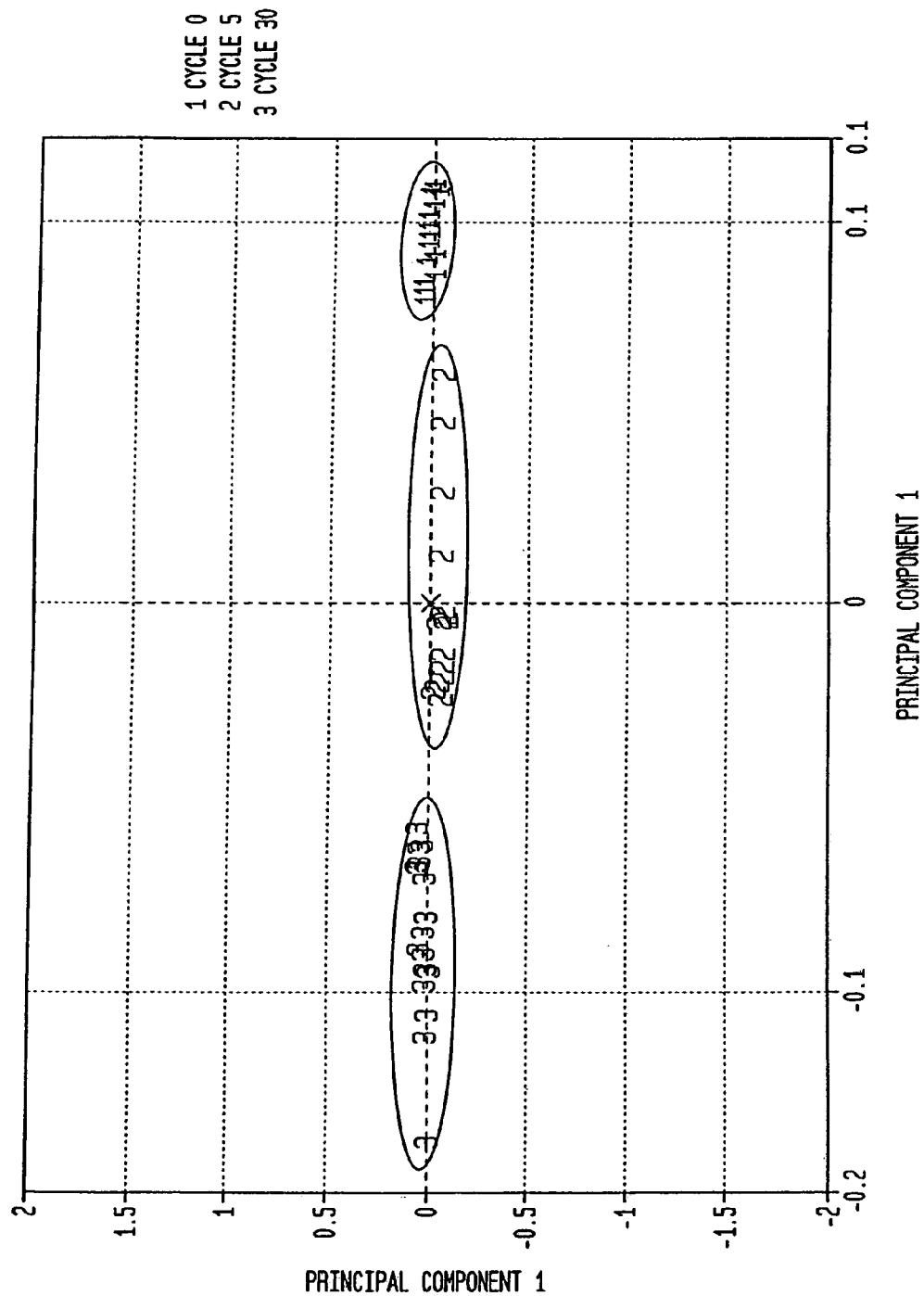
FIG. 7 shows a PCA plot of PCR reaction cycles 0, 5 and 30.

FIG. 6 and FIG. 7 show "fingerprint maps" using two different multivariate analysis methods. FIG. 6 uses DFA, one of the classification methods while FIG. 7 uses PCA, one of the discrimination methods. These show clusters representative of the PCR cycles 0, 5, and 30. The clusters are well separated showing good discrimination. There is more separation along the X axis resulting in a larger separation distance between cycles 0 and 30, than between 5 and 30. FIG. 7 shows than in this example, separation distance remains the same, but the spreading of the cluster in the second dimension is negligible.

Figure 8:
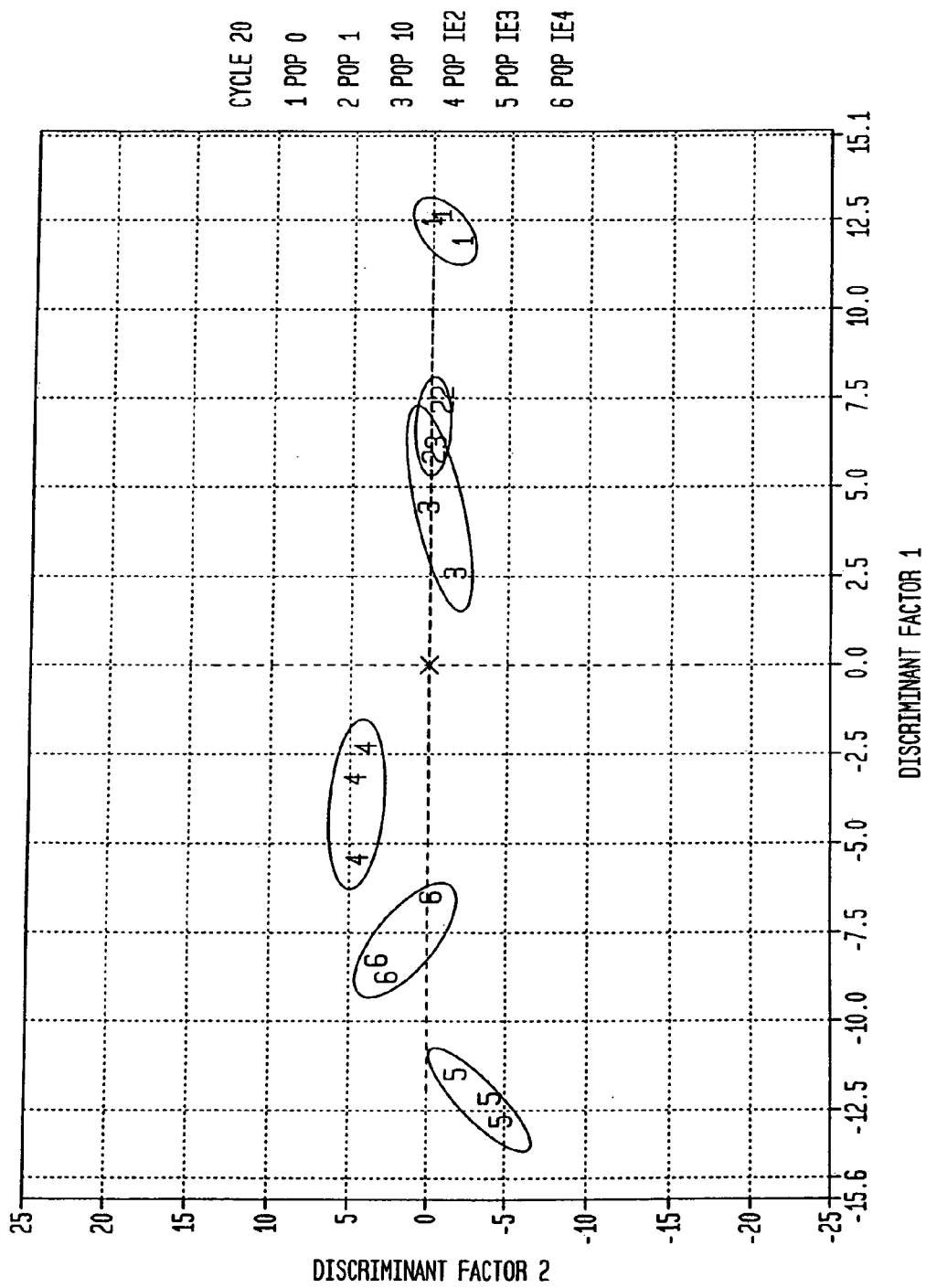
FIG. 8 shows a DFA plot of PCR reaction cycle 20 showing the discrimination between PCR populations with a resolution down to at least one copy.

FIG. 8 shows a "fingerprint map" using DFA for PCR cycle 20 with populations of 0–10,000. This plot shows very high resolution showing capability to detect a single copy (see clusters 1 and 2) during the amplification process or reaction.

The following examples will serve to further typify the nature of this invention but should not be construed as a limitation in the scope thereof, which scope is defined solely by the appended claims.

EXAMPLE I

Analysis and Control of a PCR with a Liquid Phase MSA

The data collected in the experiments whose results are shown in the enclosed figures of the present application have been acquired using the following protocol. In the experiment, plasmid DNA are used and a primer is made to the NS-1 region of a rodent parvovirus. This region is highly conserved among several different rodent viruses including: Minute Virus of Mice (MVM), Mouse Parvovirus (MPV), Kilham's Rat Virus (KRV), Toolhan's H-1 (H-1) and Rat Parvovirus (RPV). The use of plasmid DNA also allow to quantify the number of templates which are available for polymerization. For example, growing number of cycles from 1 to 30 will produce a number of copies of template DNA from 1 to 10,000. The collection of data of the present work is performed in quadruplet for each experimental condition. One of the replicate is used as a control to be run out on an agarose gel to verify that amplification has taken place. The primers used for the PCR produce a 354 bp product in the presence of template. PCR products are also checked and visualized by ethidium bromide staining for the samples cycled 30 and 40 times. Table 1 displays a list of the components and final concentrations for the parvovirus PCR performed for the present application. The final volume has been set up at 50 µL. Such small volume (typically 20–100 µL) is required as PCR requires fast energy transfers through the reaction vials. It is also within the scope of this invention to use other polymerases requiring different reaction conditions.

TABLE 1

Standard Parvovirus PCR Reaction Components

| Reagent | Components | Final Concentration |
| --- | --- | --- |
| 10X Klen Taq Buffer | Tricine-KOH (pH9.2) | 40 mM |
|  | KOAc | 15 mM |
|  | Mg(OAC)$_2$ | 3.5 mM |
|  | Bovine Serum Albumine | 75 µg/ml |
| DNTP's (dATP, dCTP, dGTP DTTP) |  | 0.2 mM |
| Primers (DNA oligomers) | Forward | 800 nM |
|  | Reverse | 800 nM |
| Water |  | 31 µL total |
| 50XadvantageKlenTaq PolyMIX | Glycerol | 1.0% |
|  | Tris-HCL (pH7.5) | 0.8 mM |
|  | KCl | 1.0 mM |
|  | (NH$_4$)$_2$SO$_4$ | 0.5 mM |
|  | EDTA | 2.0 µM |
|  | B-Mercaptoethanol | 0.1 mM |
|  | Thesit | 0.005% |
|  | Klen Taq-1 DNA polymerase W/Taq antibody | 1.1 µg total |
|  | Deep Vent Taq DNA polymerase | Traces |
| Template DNA (plasmid w/copy of target sequence) |  | 1 µL |

The temperature profile for the PCR comprised melting and annealing temperatures of 94° C. and 55° C., respectively. The reaction vials were placed in a thermal cycler (e.g., NextWave Inc.) for the appropriate number of PCR cycles.

The cycle products were analyzed by using a gas sensor array having 6 metal oxide sensors and 6 quartz crystal microbalance sensors. Typically the headspace of a sample was collected with an automated heated syringe (e.g., 37° C.) then injected and mixed with a carrier gas (e.g., zero air or humidified air @RH 10–30%) flowing to the sensor chambers. The sensor responses were typically mixed with a multiplexer and the signal output, preferably digital, was sent to an electronics means connected with a computer. The signal was then displayed and processed using mathematical algorithm, preferably multivariate analysis or any other pattern recognition method. Typical output are displayed in the various figures of the present application.

EXAMPLE II

Analysis and Control of a PCR with a Gas Phase MSA

Plasmid DNA are used and a primer which is made to the NS-1 region of a rodent parvovirus. This region is highly conserved among several different rodent viruses including: Minute Virus of Mice (MVM), Mouse Parvovirus (MPV), Kilham's Rat Virus (KRV), Toolhan's H-1 (H-1) and Rat Parvovirus (RPV). The use of plasmid DNA also allows quantification of the number of templates available for polymerization. For example, growing number of cycles from 1 to 30 will produce a number of copies of template DNA from 1 to 10,000.

Volatile organic tags chosen from chemicals such as (C2–C6) aliphatic acids, lactic acid, acetic acid, pyridine, 3-hydroxy-2-butanone, propionic acid, iso- and n-butyric acid, phenylacetaldehyde, furfuryl alcohol, isovaleric acid, α-methyl butyric acid, dimethylsulfone, n-dodecanol, n-hexadecanol, p-cresol, indole, benzaldehyde, benzoic acid, ethylene glycol, propylene glycol or any chemical derivatization procedure used in the gas-phase DNA analysis.

The collection of data of the present work has been performed in quadruplet for each experimental condition. One of the replicate was used as a control to be run out on an agarose gel to verify that amplification had taken place. The primers used for the PCR produced a 354 bp product in the presence of template. PCR products were also checked and visualized by ethidium bromide staining for the samples cycled 30 and 40 times. Table 1 displays a list of the components and final concentrations for the parvovirus PCR performed for the present application. The final volume has been set up at 50 μL. Such small volume (typically 20–100 μL) are required as PCR requires fast energy transfers through the reaction vials. It is also within the scope of this invention to use other polymerases requiring different reaction conditions.

The temperature profile for the PCR comprised melting and annealing temperatures of 94° C. and 55° C., respectively. The reaction vials were placed in a thermal cycler (e.g., NextWave Inc.) for the appropriate number of PCR cycles. The cycle products were analyzed by using a gas sensor array having 6 metal oxide sensors and 6 quartz crystal microbalance sensors. Typically the headspace of a sample was collected with an automated heated syringe (e.g., 37° C.) then injected and mixed with a carrier gas (e.g., zero air or humidified air @RH 10–30%) flowing to the sensor chambers. The sensor responses were typically mixed with a multiplexer and the signal output, preferably digital, was sent to an electronics means connected with a computer. The signal was then displayed and processed using mathematical algorithm, preferably multivariate analysis or any other pattern recognition method. Typical output are displayed in the various figures of the present application.

I claim:

1. An apparatus for analyzing at least one unlabelled biomolecule selected from the group consisting of protein, lipid, carbohydrate and nucleic acid, during a reaction process, by monitoring volatile compounds directly in-situ within a gas or vapor phase medium from the reaction, comprising:
    a multisensor array capable of detecting and discriminating more than one physico-chemical change of a gas or vapor phase of an unlabelled biomolecule or a product thereof, directly from the medium in-situ wherein the multisensor array comprises at least one metal oxide semiconductor;
    transmission means, capable of transmitting a signal between the multisensor array and a data acquisition system, capable of converting the signal into raw data;
    a computational device capable of processing at least part of the raw data using multivariate analysis to create a data set; and
    an output device capable of displaying, storing, or using the data set.

2. The apparatus according to claim 1, wherein the output device is a feedback control capable of using the data set to control a biological amplification process.

3. The apparatus according to claim 2, wherein the biomolecule is a nucleic acid, and the feedback controls a polymerase chain reaction in approximately real time.

4. An apparatus for controlling a nucleic acid replication process, comprising:
    a multisensor array capable of detecting and discriminating more than one physico-chemical change of a gas or vapor phase of a nucleic acid or a product thereof within a gas or vapor phase medium, and generating an output;
    a computational device capable of processing the output using multivariate analysis to create a data set; and
    a feedback control capable of using the data set to control the replication process.

5. The apparatus according to claim 4, wherein the multisensor array comprises at least one metal oxide semiconductor and the feedback controls a polymerase chain reaction in real time.

6. An apparatus for detecting at least one of a bacteria, bacteriophage, or a virus, comprising:
    a multisensor array capable of detecting and discriminating more than one physico-chemical change within a gas or vapor phase of an unlabelled nucleic acid extracted from the bacteria bacteriophage or virus, or unlabelled product of said nucleic acid, from a medium in situ, wherein the multisensor array comprises at least one metal oxide semiconductor;
    means for generating an output;
    a computational device capable of processing the output using multivariate analysis to create a data set; and
    an output device capable of displaying, storing, or using the data set.

7. An apparatus for analyzing at least one of a bacteria, a bacteriophage, or a virus, comprising:
    a multisensor array capable of detecting and discriminating more than one physico-chemical change within a gas or vapor phase of an unlabelled nucleic acid or an unlabelled product thereof created or modified by the bacteria, the bacteriophage, or the virus, from a medium in situ, wherein the multisensor array comprises at least one metal oxide semiconductor, and generating an output;
    a computational device capable of processing the output using multivariate analysis to create a data set; and
    an output device capable of displaying, storing, or using the data set.

* * * * *